United States Patent [19]

Aldrich et al.

[11] 4,107,303

[45] Aug. 15, 1978

[54] ANTIHYPERTENSIVE HEXAFLUOROHYDROXYISOPROPYL BENZAZEPINES AND BENZAZOCINES

[75] Inventors: Paul Edward Aldrich, Wilmington, Del.; Gilbert Harvey Berezin, West Chester, Pa.

[73] Assignee: E. I. Du Pont de Nemours and Company, Wilmington, Del.

[21] Appl. No.: 699,589

[22] Filed: Jun. 24, 1976

[51] Int. Cl.² .................... A61K 31/55; C07D 223/16
[52] U.S. Cl. .............................. 424/244; 260/239 BB; 260/283 SY; 260/289 R; 260/287 T
[58] Field of Search ................. 260/239 BB; 424/244

[56] References Cited

FOREIGN PATENT DOCUMENTS 2,552,933  6/1976  Fed. Rep. of Germany.

OTHER PUBLICATIONS

Augustine et al., "J.O.C.", 34, (1969), 1070–1075.

*Primary Examiner*—Donald G. Daus
*Assistant Examiner*—D. B. Springer

[57] ABSTRACT

Hexafluorohydroxyisopropyl: -tetrahydroquinolines, -benzazepines, and -benzazocines, such as 2,3,4,5-tetrahydro-1-(1-oxopropyl)-α,α-bis(trifluoromethyl)-1H-1-benzazepine-7-methanol useful as antihypertensives.

21 Claims, No Drawings

ANTIHYPERTENSIVE HEXAFLUOROHYDROXYISOPROPYL BENZAZEPINES AND BENZAZOCINES

BACKGROUND

This invention relates to hexafluorohydroxyisopropyl heterocyclic antihypertensives.

Allied Chemical Corporation, in British Pat. No. 1,029,048 discloses hexahalohydroxyisopropyl aryl derivatives as intermediates in the preparation of aromatic carboxylic acids.

Jones, E. S., in U.S. Pat. Nos. 3,405,177 and 3,541,152 discloses hexahalohydroxyisopropyl aromatic amines useful as intermediates in the preparation of azo dyestuffs, polyesters, polyamides, insecticides, plasticizers, and pharmaceuticals.

Gilbert, E. E., in U.S. Pat. No. 3,532,753, discloses aromatic amino derivatives of hexahaloacetone useful as insecticides.

Many current antihypertensives produce unwanted side effects because of their undesirable mechanism of action. For example, guanethidine is an adrenergic neurone blocker, mecamylamine is a ganglion blocker, phenoxybenzamine is an α-adrenergic receptor blocker, and reserpine is a catecholamine depletor. Each of these mechanisms of action is undesirable because of the serious side effects produced.

The compounds of this invention appear to lower blood pressure by a desirable mechanism of action - direct peripheral vasodilation - and, therefore have a distinct advantage over the above undesirably acting antihypertensives.

Furthermore, these compounds do not appear to produce central nervous sytem effects such as those seen with clonidine and α-methyldopa administration.

SUMMARY

According to this invention there is provided compounds of Formula I, processes for their manufacture, pharmaceutical compositions containing them, and methods of using them to treat hypertension in mammals.

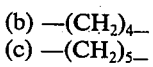

Formula I where
$R_1$ and $R_2$ taken together =

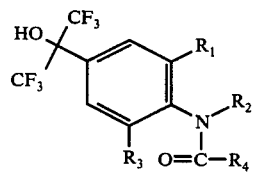

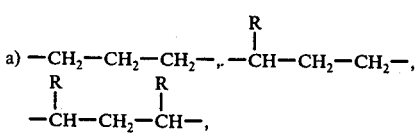

(b) $-(CH_2)_4-$
(c) $-(CH_2)_5-$
where
R = methyl or ethyl;
$R_3$ = H, methyl, or ethyl; and
$R_4$ = $C_1-C_5$ carbons which can be straight-chained, branched-chained, or alicyclic.

DETAILED DESCRIPTION

Preferred Compounds

Compounds preferred because of their high activity are the benzazepines: those in which $R_1$ $R_2$ taken together are $-(CH_2)_4-$.

Most preferred are the following compounds: 2,3,4,5-tetrahydro-1-(1-oxopropyl-α, α-bis(trifluoromethyl)-1H-1-benzazepine-7-methanol. 1-(cyclopropylcarbonyl)-2,3,4,5-tetrahydro-α,α-bis(trifluoromethyl)-1H-1-benzazepine-7-methanol. 1-acetyl-2,3,4,5-tetrahydro-α,α-bis-(trifluoromethyl)-1H-1-benzazepine-7-methanol. 2,3,4,5-tetrahydro-1-(2-methyl-1-oxopropyl)-α,α-bis(trifluoromethyl)-1H-benzazepine-7-methanol.

Synthesis

Intermediates are prepared as shown in the following general reaction:

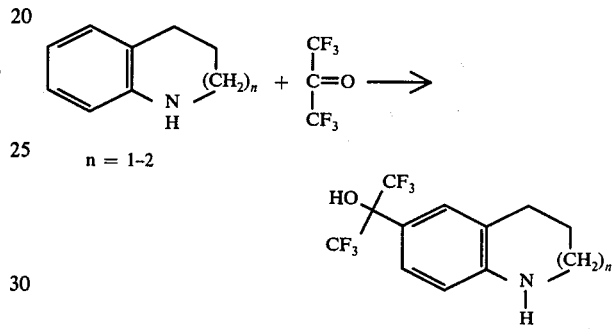

n = 1-2

The reaction is conducted in a sealed pressure reactor at temperatures from 80°-200° C. It can also be conducted in a refluxing solvent, such as benzene or toluene, in a flask with hexafluoroacetone sesquihydrate. Acidic catalysts such as $AlCl_3$, $BF_3$, or p-toluenesulfonic acid can be used but C not necessary. Reaction time is usually 4-12 hours. A temperature of 100°-120° and use of 1-5 mole percent of $AlCl_3$ are preferred.

The amine starting materials are either known in the art or easily prepared from those known in the art. Methods for making the various ring systems, however, are outlined as follows:

Tetrahydroquinolines

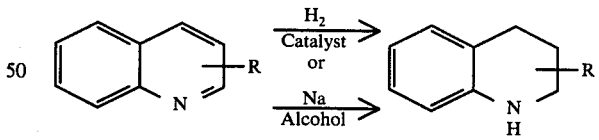

See Elderfield, R. C., *Heterocyclic Compounds* Vol. 4, John Wiley & Sons, Inc. New York, N.Y. (1952) p.1.

*Benzazepines and Benzazocines*

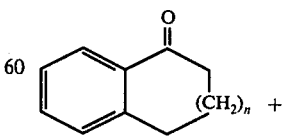

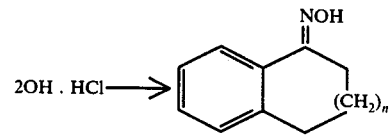

In the reaction scheme outlined, ketone (6,7,8,9-tetrahydro-5H-benzocyclohepten-5-one or 3,4-dihydro-1(2H)-naphthalenone) is contacted with hydroxylamine hydrochloride to give the corresponding oxime.

The oxime is rearranged by treatment with polyphosphoric acid to give either 2,3,4,5-tetrahydro-1H-1-benzazepin-2-one or 3,4,5,6-tetrahydro-1-benzazocin-2(1H)-one.

Reduction of these lactams with LiAlH$_4$ gives 2,3,4,5-tetrahydro-1H-1-benzazepine or 1,2,3,4,5,6-hexahydro-1-benzazecine.

The ketone starting materials for the parent systems discussed above are known in the art and are commercially available. The following two starting materials, however, are not so well known; their preparation is therefore discussed. 3,4-Dihydro-8-methyl-1-(2H)-naphthalenone and 3,4-dihydro-8-ethyl-1-(2H)-naphthalenone are prepared by oxidation of the corresponding tetrahydronaphthalenes with chromic acid, followed by purification by gas-liquid chromotography.

See Burnham, J. W. et al. *J. Org. Chem.*, 39 (10), 1416 (1974). 6,7,8,9-Tetrahydro-4-methyl-5H-benzocyclohepten-5-one and 4-ethyl-6,7,8,9-tetrahydro-5H-benzocyclohepten-5-one are prepared by reaction of a benzyne with an enolate of cyclopentanone; the desired product can be separated from side-products by gas-liquid chromatography.

See Caubere, P. et al., *Bull. Soc. Chim. Fr.* (12) Pt. 2, 3493 (1973).

Compounds of this invention are prepared as shown in the following general reaction:

where
$n = 1 = 3$;
R and R' independently = H, methyl, or ethyl when $n = 1$;
R and R' = hydrogen when $n = 2$ or 3; and
R$_3$ = H, methyl, and ethyl; and
R$_4$ = C$_1$—C$_5$ carbons which can be straight-chained, branched-chained, or alicyclic.

The amine starting material is heated with the appropriate acid chloride or acid anhydride in an aprotic solvent or with water plus base.

Under preferred conditions the reactants are heated at 80°–110° C in benzene or toluene until analysis by thin layer chromatography indicates the reaction is complete. The mixture is cooled, solvent removed, and residual material purified by recrystallization.

The following examples further illustrate the methods for preparing these compounds. All parts are by weight and all temperatures are in degrees centigrade unless otherwise indicated.

EXAMPLE 1

2,3,4,5-Tetrahydro-1-(1-oxopropyl)-α,α-bis(trifluoromethyl)-1H-1-benzazepine-7-methanol.

To a solution of 7.0 gm (0.051 mole) of propionic anhydride in 200 ml of benzene is added 15.6 g (0.050 mole) of α,α-bis(trifluoromethyl)-2,3,4,5-tetrahydro-1H-1-benzazepine-7-methanol. The solution is stirred and heated at reflux under nitrogen for eighteen hours, then cooled and evaporated at reduced pressure. The solid residue is recrystallized from chlorobutane to give 15 gm of α,α-bis(trifluoromethyl)-1-(1-oxypropyl)-2,3,4,5-tetrahydro-1H-1-benzazepine-7-methanol, m.p. 150°–153° C.

Anal. Calc'd. for: C$_{16}$H$_{17}$NO$_2$F$_6$: C, 52.04; H, 4.64; N, 3.79; Found: C, 51.89; H, 4.79; N. 3.68.

EXAMPLES 2–29

Using the procedure of Example 1, the following compounds can be made using the appropriate starting materials which are shown.

-continued
| Starting Materials | Products |
|---|---|
| 3. 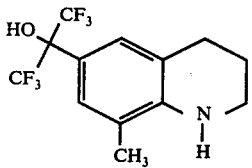 + 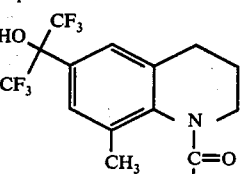 | m.p. 144–145° 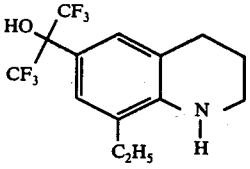 |
| 4. 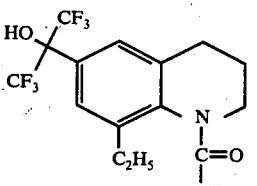 | 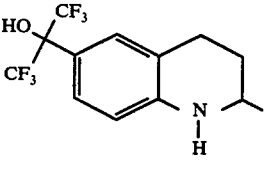 |
| 5. 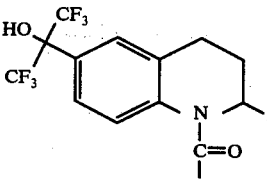 | 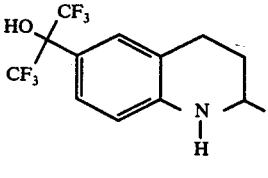 |
| 6. 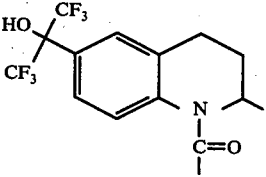 | 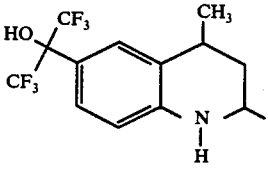 |
| 7. 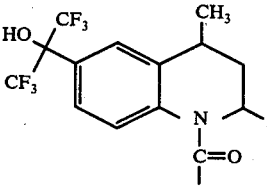 | 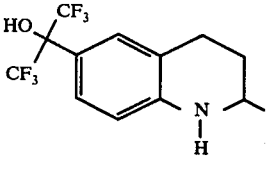 |
| 8. 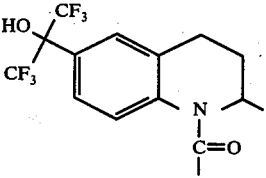 | 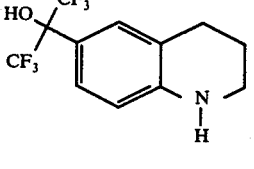 |
| 9. 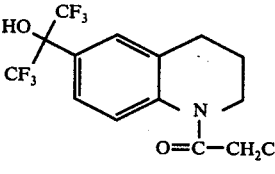 | 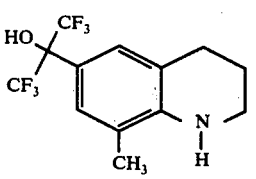 |
| 10. 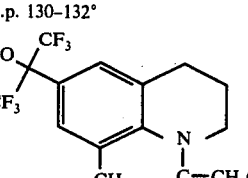 | m.p. 130–132° |

-continued
| Starting Materials | Products |
|---|---|
| 11. 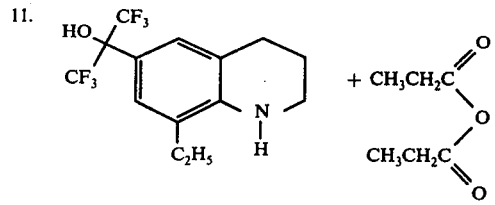 | 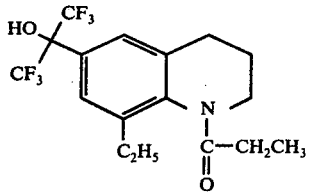 |
| 12. 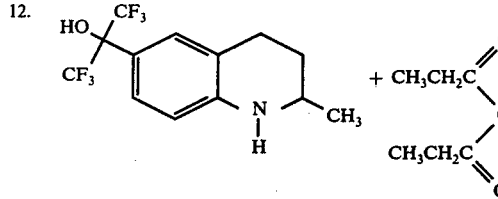 | 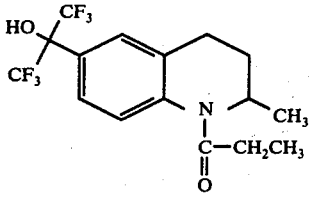 |
| 13. 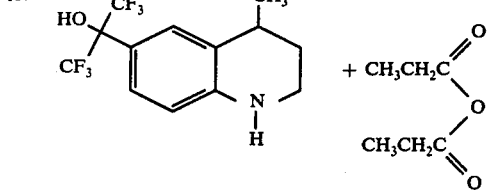 | 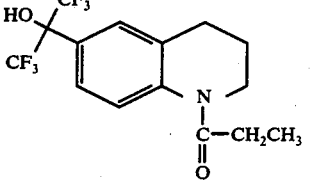 |
| 14. 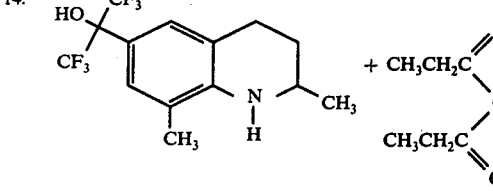 | 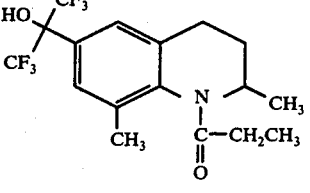 |
| 15. 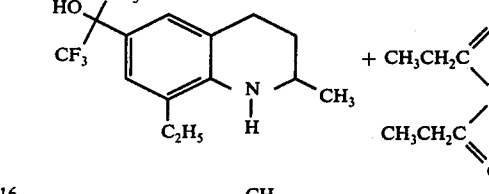 | 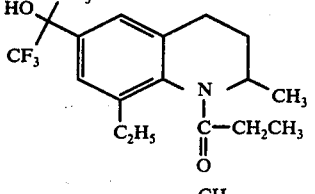 |
| 16. 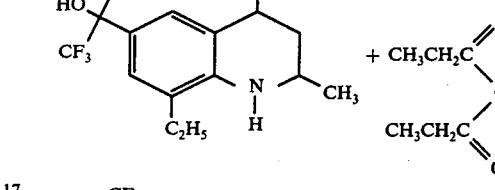 | 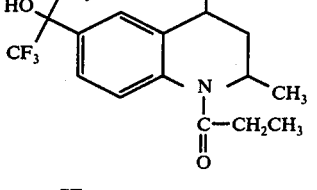 |
| 17. 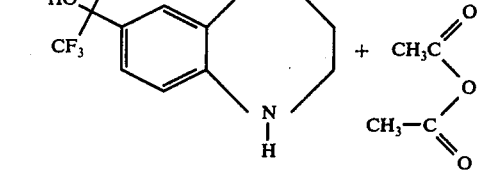 | 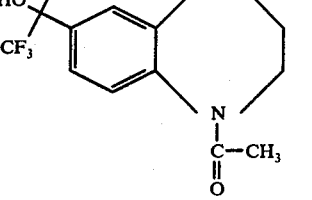  m.p. 203–204° |
| 18. 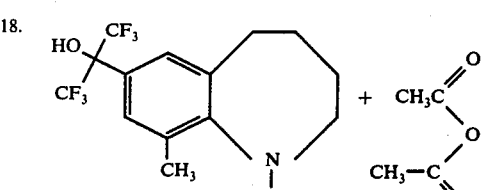 | 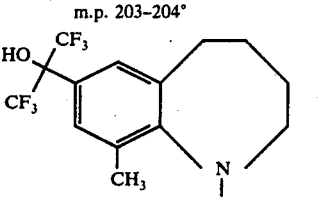 |

| Starting Materials | Products |
|---|---|
| 19. [benzazepine with HO-C(CF₃)₂ and C₂H₅ substituents, NH] + (CH₃CO)₂O | [N-acetyl product with HO-C(CF₃)₂ and C₂H₅] |
| 20. [benzazepine with HO-C(CF₃)₂ and CH₃ substituents, NH] + (CH₃CH₂CO)₂O | [N-propanoyl product with HO-C(CF₃)₂ and CH₃] |
| 21. [benzazepine with HO-C(CF₃)₂ and C₂H₅ substituents, NH] + (CH₃CH₂CO)₂O | [N-propanoyl product with HO-C(CF₃)₂ and C₂H₅] |
| 22. [benzazepine with HO-C(CF₃)₂, NH] + (CH₃CH₂CH₂CO)₂O | [N-butanoyl product] m.p. 137–139° |
| 23. [benzazepine with HO-C(CF₃)₂ and CH₃ substituents, NH] + (CH₃CH₂CH₂CO)₂O | [N-butanoyl product with HO-C(CF₃)₂ and CH₃] |
| 24. [benzazocine with HO-C(CF₃)₂, NH] + (CH₃CO)₂O | [N-acetyl benzazocine product] m.p. 202–204° |
| 25. [benzazocine with HO-C(CF₃)₂ and CH₃, NH] + (CH₃CO)₂O | [N-acetyl benzazocine product with CH₃] |

4,107,303
-continued
| Starting Materials | Products |
|---|---|
| 26. 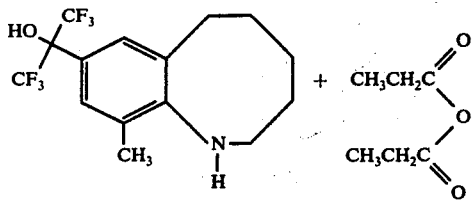 | 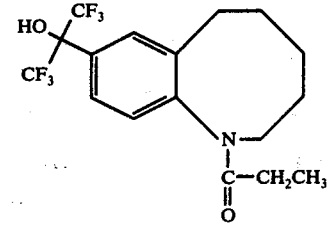<br>m.p. 184–186° |
| 27. 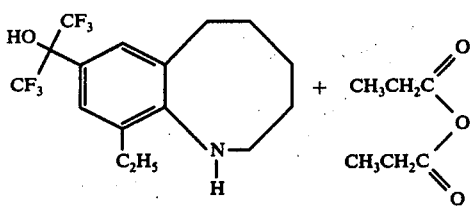 | 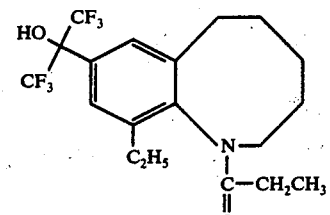 |
| 28. 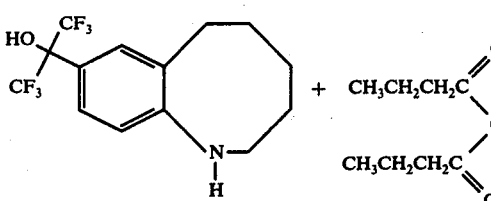 | 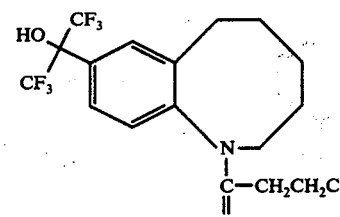<br>m.p. 152–155° |
| 29. 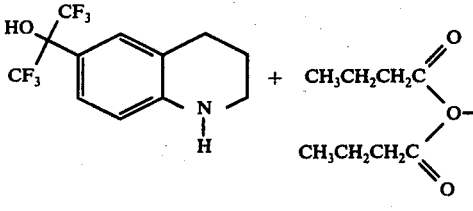 | 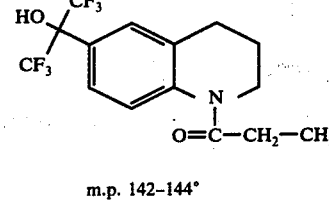<br>m.p. 142–144° |
| 30. 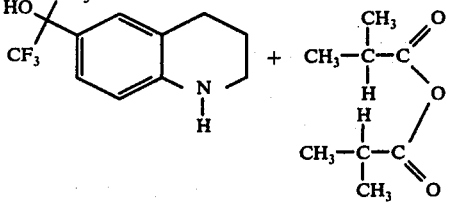 | 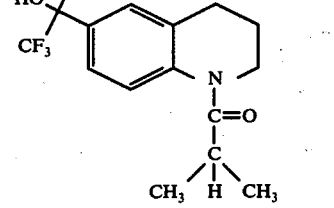 |
| 31. 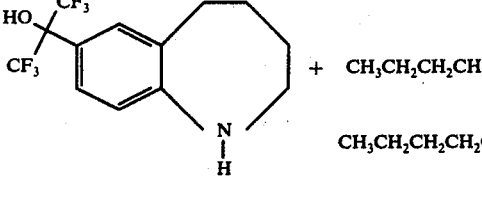 | 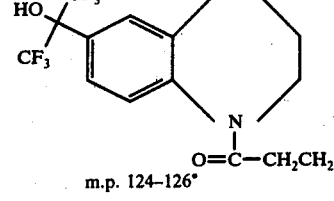<br>m.p. 124–126° |
| 32. 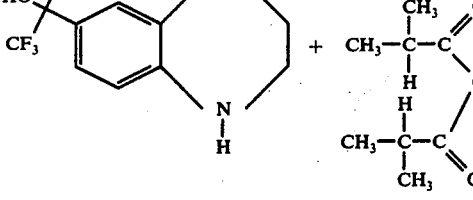 | 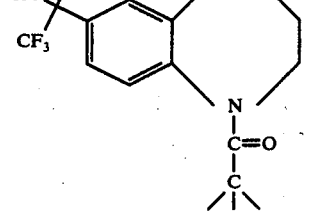<br>m.p. 180–182° |

| Starting Materials | | Products |
|---|---|---|
| 33. 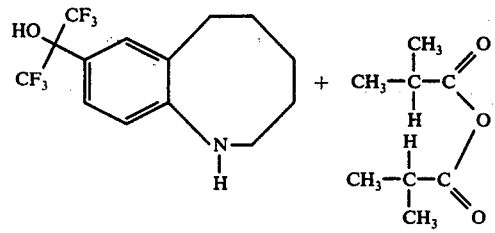 | 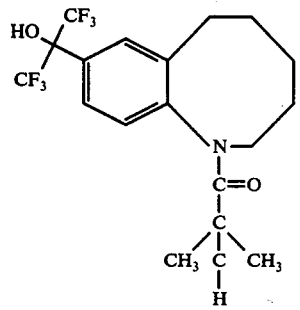 | |

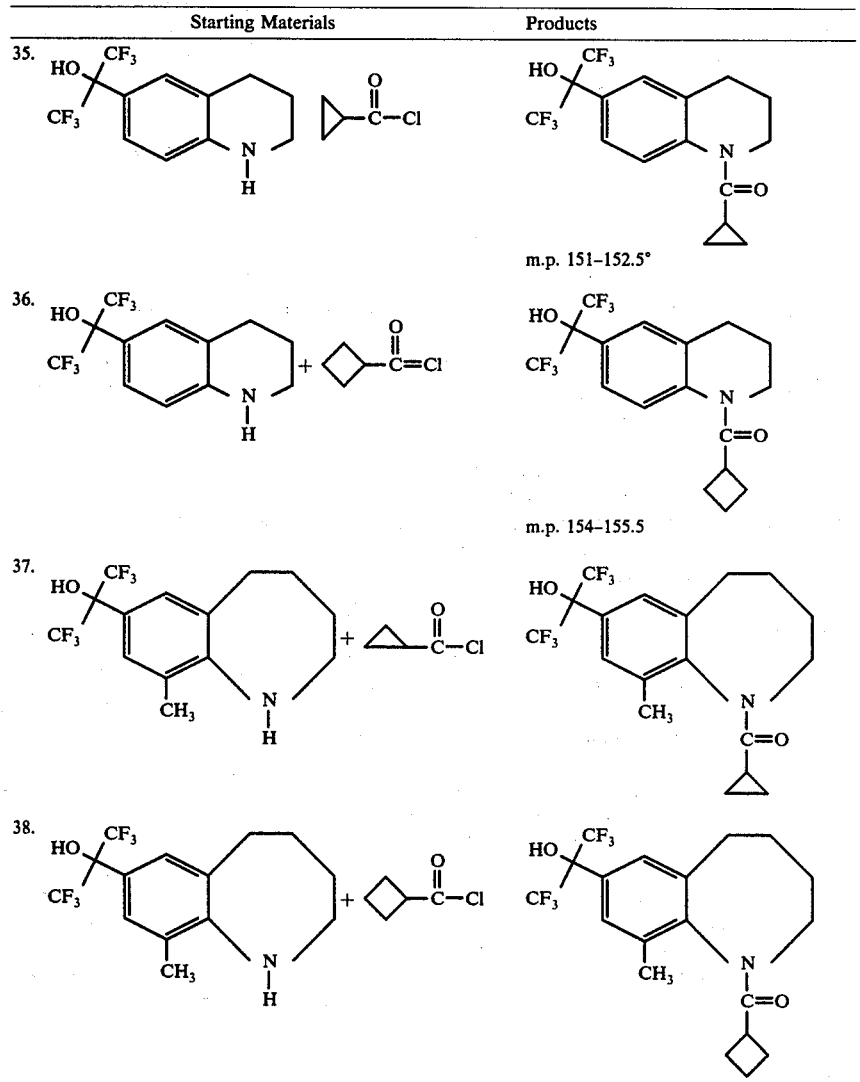

EXAMPLE 34

1-(cyclopropylcarbonyl)-2,3,4,5-tetrahydro-α,α-bis(trifluoromethyl)-1H-benzazepine-7-methanol.

To 200 ml dry toluene is added 6.3 g (0.020 mole) α,α-bis(trifluoromethyl)-2,3,4,5-tetrahydro-1H-1-benzazepine-7-methanol and 3.0 g (0.025 mole) cyclopropane carboxylic acid chloride. The solution is stirred and heated at reflux under nitrogen for sixteen hours, then cooled and evaporated at reduced pressure. The residual solid is recrystallized from chlorobutane to give 5.0 g, m.p. 165°–167°.

Anal Calc'd. for: $C_{17}H_{17}F_6NO_2$: C, 53.54; H, 4.46; N, 3.67. Found: C, 53.43; H, 4.65; N, 3.75.

-continued

| Starting Materials | Products |
|---|---|
| 39. | 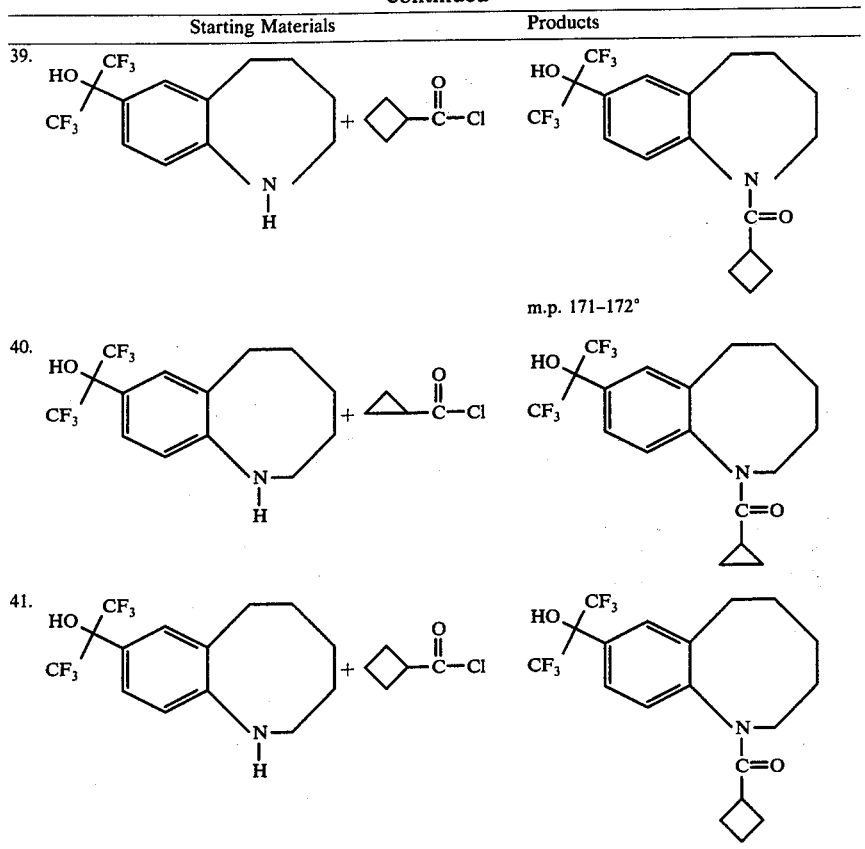 |
| 40. | |
| 41. | | m.p. 171–172°

Dosage Forms

The antihypertensive agents of this invention can be administered to treat hypertension by any means that produces contact of the active agent with the agent's site of action in the body of a mammal. The can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.02 to 50 milligrams per kilogram of body weight. Ordinarily 0.1 to 40 milligrams per kilogram per day, and preferably 0.2 to 20 milligrams per kilogram per day given in divided doses 2 to 4 times a day or in sustained release form is effective to obtain desired results. For the more potent compounds the daily dosage ranges are 0.02 to 20 milligrams per kilogram, preferably 0.1 to 15 milligrams per kilogram, and more preferably 0.2 to 10 milligrams per kilogram.

Dosage forms (compositions) suitable for internal administration contain from about 1.0 milligrams to about 100 milligrams of active ingredient per unit. In these pharmaceutical compositions the active ingredient will ordinarily be present in an amount of about 0.5 – 95% by weight based on the total weight of the composition.

The active ingredient can be administered orally in solid dosage forms such as capsules, tablets, and powders, or in liquid dosage forms such as elixirs, syrups, and suspensions; it can also be administered parenterally, in sterile liquid dosage forms.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 5 milligrams of powdered active ingredient, 150 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 2 milligrams of the active ingredient. The capsules are washed in petroleum ether and dried.

Tablets

A large number of tablets are prepared by conventional procedures so that the dosage unit is 15 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Suspension

An aqueous suspension is prepared for oral administration so that each 5 milliliters contain 10 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Utility

The antihypertensive activity of the compounds of this series is detected and compared in a procedure using DOCA hypertensive rats, which shows good correlation with human efficacy.

Rats are made hypertensive by subcutaneous implantation of pellets of desoxycorticosterone acetate (DOCA) and by giving saline solution to drink essentially according to the method described by Sturtevant [Annals of Internal Medicine, 49, 1281 (1958)]. Graded dose levels of each compound are administered orally to groups of 8 hypertensive rats. The compound is prepared in an aqueous polyvinyl alcohol/acacia vehicle and administered at a volume to body weight ratio of 5.0 ml/kg. Sixteen hypertensive rats receiving the aqueous vehicle by the same route serve as controls for each test. At various intervals of time after treatment, usually 90 minutes, the systolic arterial blood pressure of each rat is determined by a modification of the microphone-manometer technique [Friedman, M. and Freed, S.C., Proc. Soc. Exp. Biol, and Med., 70, 670 (1949)]. That dose of compound which produces a 30 mm mercury (mm Hg) reduction in blood pressure when compared to the mean systolic arterial blood pressure of the control animals is then determined (Effective Dose 30).

When tested by this procedure the following $ED_{30}$ dosages were determined.

ANTIHYPERTENSIVE $ED_{30}$'s

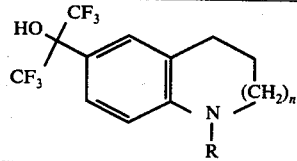

| COMPOUND | | |
|---|---|---|
| n | R | $ED_{30}$ (mg/kg) |
| 1 | 1-oxopropyl | 9.0 |
| 1 | acetyl | 14 |
| 2 | 1-oxopropyl | 0.52 |
| 2 | acetyl | 1.3 |
| 2 | 1-oxobutyl | 3.8 |
| 3 | acetyl | 4.5 |
| 3 | 1-oxopropyl | 4.0 |
| 3 | 1-oxobutyl | 2.9 |
| 2 | 1-(cyclopropylcarbonyl) | 1.1 |
| 2 | 1-oxo-2-butenyl | ~50 |
| 2 | 2-methyl-1-oxopropyl | 1.4 |

What is claimed is:

1. A compound of the formula

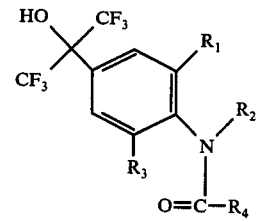

where
$R_1$ and $R_2$ taken together $= -(CH_2)_4-$ or $-(CH_2)_5-$
where
R = methyl or ethyl;
$R_3$ = H, methyl, or ethyl; and
$R_4$ = $C_1$–$C_5$ carbons which are saturated and straight-chained, branched-chained, or alicyclic.

2. The compound of claim 1 wherein $R_1$ and $R_2$ taken together are $-(CH_2)_5-$.

3. The compound of claim 1 wherein $R_1$ and $R_2$ taken together are $-(CH_2)_4-$.

4. The compound of claim 3: 2,3,4,5-tetrahydro-1-(1-oxopropyl)-α,α-bis(trifluoromethyl)-1H-1-benzazepine-7-methanol.

5. The compound of claim 3: 1-(cyclopropylcarbonyl)-2,3,4,5-tetrahydro-α,α-bis(trifluoromethyl)-1H-1-benzazepine-7-methanol.

6. The compound of claim 3: 1-acetyl-2,3,4,5-tetrahydro-α,α-bis-(trifluoromethyl)-1H-1-benzazepine-7-methanol.

7. The compound of claim 3: 2,3,4,5-tetrahydro-1-(2-methyl-1-oxopropyl)-α,α-bis(trifluoromethyl)-1H-benzazepine-7-methanol.

8. A pharmaceutical composition comprising a pharmaceutically suitable carrier and an effective antihypertensive amount of a compound of claim 1.

9. A pharmaceutical composition comprising a pharmaceutically suitable carrier and an effective antihypertensive amount of a compound of claim 2.

10. A pharmaceutical composition comprising a pharmaceutically suitable carrier and an effective antihypertensive amount of a compound of claim 3.

11. A pharmaceutical composition comprising a pharmaceutically suitable carrier and an effective antihypertensive amount of the compound of claim 4.

12. A pharmaceutical composition comprising a pharmaceutically suitable carrier and an effective antihypertensive amount of the compound of claim 5.

13. A pharmaceutical composition comprising a pharmaceutically suitable carrier and an effective antihypertensive amount of the compound of claim 6.

14. A pharmaceutical composition comprising a pharmaceutically suitable carrier and an effective antihypertensive amount of the compound of claim 7.

15. A method of treating hypertension in a mammal which comprises administering to the mammal an effective antihypertensive amount of a compound of claim 1.

16. A method of treating hypertension in a mammal which comprises administering to the mammal an effective antihypertensive amount of a compound of claim 2.

17. A method of treating hypertension in a mammal which comprises administering to the mammal an effective antihypertensive amount of a compound of claim 3.

18. A method of treating hypertension in a mammal which comprises administering to the mammal an effective antihypertensive amount of the compound of claim 4.

19. A method of treating hypertension in a mammal which comprises administering to the mammal an effective antihypertensive amount of the compound of claim 5.

20. A method of treating hypertension in a mammal which comprises administering to the mammal an effective antihypertensive amount of the compound of claim 6.

21. A method of treating hypertension in a mammal which comprises administering to the mammal an effective antihypertensive amount of the compound of claim 7.

* * * * *